(12) United States Patent
Kavusi et al.

(10) Patent No.: US 9,188,585 B2
(45) Date of Patent: Nov. 17, 2015

(54) DEVICE AND METHOD FOR INDIRECT MODULATION OF DETECTION ENVIRONMENT

(75) Inventors: Sam Kavusi, Menlo Park, CA (US); Yi Wei Chen, Stanford, CA (US); Michael Chen, Fremont, CA (US); Christoph Lang, Cupertino, CA (US)

(73) Assignee: Robert Bosch GmbH, Stuttgart (DE)

( * ) Notice: Subject to any disclaimer, the term of this patent is extended or adjusted under 35 U.S.C. 154(b) by 1017 days.

(21) Appl. No.: 12/779,687

(22) Filed: May 13, 2010

(65) Prior Publication Data

US 2011/0278258 A1 Nov. 17, 2011

(51) Int. Cl.
*G01N 1/00* (2006.01)
*G01N 33/543* (2006.01)

(52) U.S. Cl.
CPC .... *G01N 33/54306* (2013.01); *G01N 33/54366* (2013.01); *G01N 33/54393* (2013.01); *Y10T 436/25* (2015.01)

(58) Field of Classification Search
CPC ............... G01N 33/54306; G01N 33/54393; G01N 33/54366; Y10T 436/25
USPC ......... 436/180; 422/107, 108, 501–504, 68.1, 422/402–404; 435/287.1, 288.4, 288.5
See application file for complete search history.

(56) References Cited

U.S. PATENT DOCUMENTS

| | | | |
|---|---|---|---|
| 6,540,891 B1 * | 4/2003 | Stewart et al. | 204/403.14 |
| 7,348,783 B1 | 3/2008 | Hsiung et al. | |
| 2003/0232399 A1 | 12/2003 | Robertson et al. | |
| 2005/0266478 A1 * | 12/2005 | Huang et al. | 435/6 |
| 2006/0019299 A1 | 1/2006 | Kang et al. | |
| 2006/0019404 A1 | 1/2006 | Blatt et al. | |
| 2006/0108236 A1 | 5/2006 | Kasielke et al. | |
| 2007/0097364 A1 | 5/2007 | Shepard et al. | |

FOREIGN PATENT DOCUMENTS

| | | |
|---|---|---|
| JP | 2008249423 A | 10/2008 |
| JP | 2013508682 A | 3/2013 |
| WO | 2011047020 A1 | 4/2011 |

OTHER PUBLICATIONS

International Search Report in corresponding PCT application (i.e., PCT/US2011/035882) mailed Aug. 23, 2011 (15 pages).

Saaem I et al: "Preliminary studies on the rapid detection of staphylococcus aureas using a microfluidic device and nanopatterned hydrogels", Bioengineering Conference, 2007. NEBC '07. IEEE 33rd Annual Northeast, IEEE, Piscataway, NJ, USA, Mar. 1, 2007, pp. 234-235, XP031198175, DOI: DOI: 10.1109/NEBC.2007. 4413364 ISBN: 978-1-4244-1032-3 p. 234, right-hand column, paragraph 1-paragraph 2 (2 pages).

(Continued)

*Primary Examiner* — Shogo Sasaki
(74) *Attorney, Agent, or Firm* — Maginot Moore & Beck LLP (57) ABSTRACT

A system and method of indirectly modifying an environmental condition at a test site in one embodiment includes providing a test site on a substrate, providing a first activatable stimulant at the test site, providing an actuator configured to activate the first activatable stimulant at the test site, controlling the actuator to activate the first activatable stimulant, and modifying the local chemical environment at the test site with the first activated stimulant.

13 Claims, 6 Drawing Sheets

(56) References Cited

OTHER PUBLICATIONS

Cox J D et al: "Surface passivation of microfluidic device to glial cell adhesion: a comparison of hydrophobic and hydrophilic SAM coatings". Biomaterials, Elsevier Science Publisher BV., Barking, GB, vol. 23, No. 3, Feb. 1, 2002, pp. 929-935, XP004348108, ISSN: 0142-9612, DOI: DOI:10.1016/S0142-9612(01) 00205-8 p. 934, right-hand column, paragraph 1-paragraph 2 (8 pages).
Ye et al: "Deposition temperature effect on release rate of indomethacin microcrystals from microcapsules of layer-by-layer assembled chitosan and alginate multilayer films", Journal of Controlled Release, Elsevier, Amsterdam, NL, vol. 106, No. 3, Sep. 2, 2005, pp. 319-328, XP005038452, ISSN: 0168-36659 the whole document.
M.L. O'Grad, K. Parker, "Dynamic Control of Protein-Protein Interactions," Langmuir, vol. 24 (1), pp. 316-322, 2008 (8 pages).
N. Ohmura, Y. Tsukidate, H. Shinozaki, S.J. Lackie, and H. Saiki, "Combinational Use of Antibody Affinities in an Immunoassay for Extension of Dynamic Range and Detection of Multiple Analytes, "Analytical Chemistry, vol. 75, No. 1, pp. 104-110, 2003 (7 pages).
Ulrich Rant et al., "Switchable DNA interfaces for the highly sensitive detection of label-free DNA targets," Proceedings of the National Academy of Sciences 104, No. 44 (Oct. 30, 1977): 17364-17369.
Roy et al., "Effect of pressure on antigen-antibody complexes: modulation by temperature and ionic strength," Molecular Immunology 36, pp. 1149-1158, 1999 (10 pages).
M Schena et al., "Quantitative monitoring of gene expression patterns with a complementary DNA microarray," Science (New York, N.Y.) 270, No. 5235 (Oct. 20, 1995): 467-470 (4 pages).
Selby, "Interference in immunoassay," Annals of Clinical Biochemistry, 36, pp. 704-721, 1999 (18 pages).
Robert F. Service, "Proteomics: Proteomics Ponders Prime Time," Science 321, No. 5897 (Sep. 26, 2008): 1758-1761.
S. Skirtach, C. Dejugnat, D. Braun, A. Susha, A. Rogach, W. Parach, H. Mohwald, and G. Sukhorukov, "The role of metal nanoparticles in remote release of encapsulated materials," Nano Letters, vol. 5, pp. 1371-1377, 2005.
R.G. Sosnowski et al., "Rapid determination of single base mismatch mutations in DNA hybrids by direct electric field control," Proceedings of the National Academy of Sciences of the United States of America 94, No. 4 (Feb. 18, 1997).
Ian Y. Wong, Matthew J. Footer, and Nicholas A. Melosh, "Electronically Activated Actin Protein Polymerization and Alignment," Journal of the American Chemical Society 130, No. 25 (Jun. 1, 2008): 7908-7915 (8 pages).
Wong et al., "Dynamic control of biomolecular activity using electrical interfaces," The Royal Society of Chemistry, 3, pp. 267-274, 2007 (8 pages).
M.L. Yarmush, K.P. Antonsen, S. Sundaram, and D.M. Yarmush, "Immunoadsorption: Strategies for Antigen Elution and Production of Reusable Adsorbents," Biotechnology Progress, vol. 8, No. 3, pp. 168-178, 1992.
Stephen F. Kingsmore, "Multiplexed protein measurement: technologies and applications of protein and antibody arrays," Nat. Reviews. Drug Discovery 5, No. 4 (Apr. 2006): 310-320 (23 pages).
Lance A. Liotta et al., "Protein microarrays: Meeting analytical challenges for clinical applications," Cancer Cell 3, No. 4 (Apr. 2003): 317-325 (9 pages).
Liron et al., Voltage-induced inhibition of antigen-antibody at conducting optical waveguides, Biosensors and Bioelectrics, 17, pp. 489-494, 2002 (6 pages).
Asanov et al., Regenerable Biosensor Platform: A Total Internal Reflection Flourescence Cell with Electrochemical Control; Analytical Chemistry, vol. 70, No. 6, pp. 1156-1163, 1998, (8 pages).
Bergveld, Development of an Ion sensitive solid-state device for neurophysiological measurements, IEEE Transactions on Biomedical Engineering, BME-17, pp. 70-71, 1970.
B. DeGeest, "Intracellularly degradable polyelectrolyte microcapsules," Adv Mater, vol. 18, pp. 1005-1009, 2006.
B. DeGeest, A. Skirtach, A. Manedov, A. Antipov, N. Kotov, S. DeSmedt, and G. Sukhorukov, "Ultrasound-triggered release from multilayered capsules," Small, vol. 3, pp. 804-808, 2007.
Patrick Domnanich, Ursula Sauer, Johanna Pultar, and Claudia Preininger, "Protein microarray for the analysis of human melanoma biomarkers," Sensors and Actuators B: Chemical, vol. 139, pp. 2-8 (2009).
E. Donath, G. Sukhorukov, F. Caruso, S. Davis, and H. Mohwold, "Novel hollow polymer shells by colloid-templated assembly of polyelectrolytes," Angew Chem, Int Ed, vol. 37, pp. 2201-2205, 1998.
A.P. Drabovich, V. Okhonin, M. Berezovski, and S.N. Krylov, Smart Aptamers Facilitate Multi-Probe Affinity Analysis of Proteins with Ultra-Wide Dynamic Range of Measured Concentrations, Journal of the American Chemical Society, vol. 129, No. 23, pp. 7260-7261 and S1-S5, 2007 (2 pages plus 5 pages of Supporting Materials).
CF Edman et al., "Electric field directed nucleic acid hybridization on microchips," Nucl. Acids Res. 25, No. 24 (Dec. 15, 1997): 4907-4914.
M. Ferrari, "Cancer nanotechnology: Opportunities and challenges," Nat Rev Cancer, vol. 5, pp. 161-171, 2005.
J.J. Gooding et al., "Electrochemical modulation of antigen-antibody binding," Biosensors and Bioelectronics, vol. 20, No. 2, pp. 260-268, 2004.
Heaton et al., Electrostatic surface plasmon resonance: Direct electric field-induced hybridization and denaturation in monolayer nucleic acid films and label-free discrimination of base mismatches, Proceedings of National Academy of Sciences of the U.S.A., vol. 98, No. 7, pp. 3701-3704, 2001, (4 pages).
T. Hizawa et al., "Fabrication of a two-dimensional pH image sensor using a charge transfer technique," Sensors and Actuators B 117, pp. 509-515, 2006.
Leroy Hood et al., "Systems Biology and New Technologies Enable Predictive and Preventative Medicine," Science 306, No. 5696 (Oct. 22, 2004): 640-643.
G. Ibarz, L. Dahne, E. Donath, and H. Mohwald, "Resealing of polyelectrolyte capsule after core removal," Macromol Rapid Commun, vol. 23, pp. 474-478, 2002.
Jackola et al., "Entropy-favored human antibody binding reactions with a non-infectious antigen," Molecular Immunology, 45, pp. 1494-1500, 2008 (7 pages).
Wong et al., "Directed Hybridization and Melting of DNA Linkers using Counterion-Screened Electric Fields," Nano Letters, 2009, pp. 3521-3526, vol. 9, No. 10, The American Chemical Society, USA (6 pages).
English Translation of Japanese Office Action and Search Report corresponding to Japanese Patent Application No. 2013-510234, dated Jan. 22, 2015 (3 pages).

\* cited by examiner

DEVICE AND METHOD FOR INDIRECT MODULATION OF DETECTION ENVIRONMENT

FIELD

This invention relates to diagnostic tests and more specifically to affinity based diagnostic tests.

BACKGROUND

Diagnostic tests that can be performed at the point of care of an individual, such as at the bedside of a patient, at a care provider location, or at the home of the patient, are becoming increasingly popular. The promise of such diagnostic tests is described, for example, by Leroy Hood et al., "Systems Biology and New Technologies Enable Predictive and Preventative Medicine," *Science* 306, no. 5696 (Oct. 22, 2004): 640-643. Depending upon the particular diagnostic test, the substance tested may be human body fluids such as blood, serum, saliva, biological cells, urine, or other biomolecules. Diagnostic tests are not, however, limited to biomolecules since testing may be further desired on consumables such as milk, baby food, or water.

Many diagnostic testing devices incorporate affinity based sensors which are considered to be the state-of-the-art in detection of biomarkers. Affinity based sensors function according to a "key-lock" principal in which a molecule with very high association factor to the marker of interest is used for detection. For example, a pregnancy test kit may incorporate a monoclonal antibody specific to a β-subunit of hCG (βhCG). The antibody is conjugated with a tag, e.g., gold, latex, or fluorophore, which is used for detection. If the targeted molecule binds with the conjugated antibody, the tagged key-lock pair will be detectable such as by a visible test line.

Figure 1:
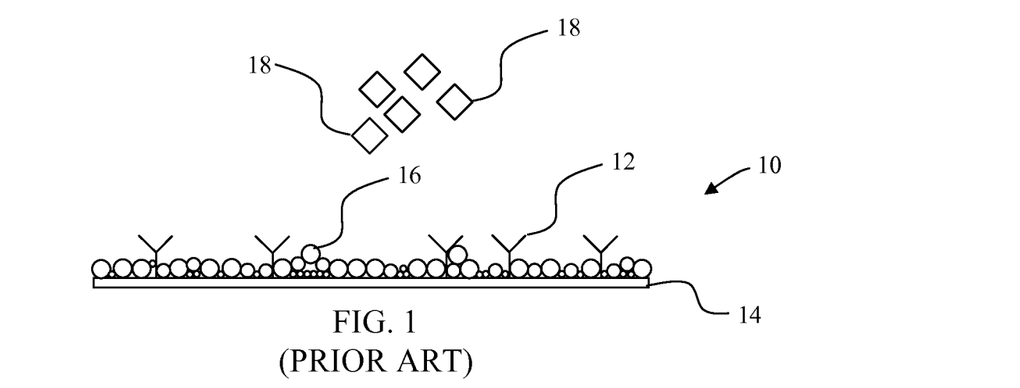
FIG. 1 depicts a schematic of a prior art test site within an ELISA array with an antibody and blockers formed on a substrate as a sample is added to the test site.
Figure 2:
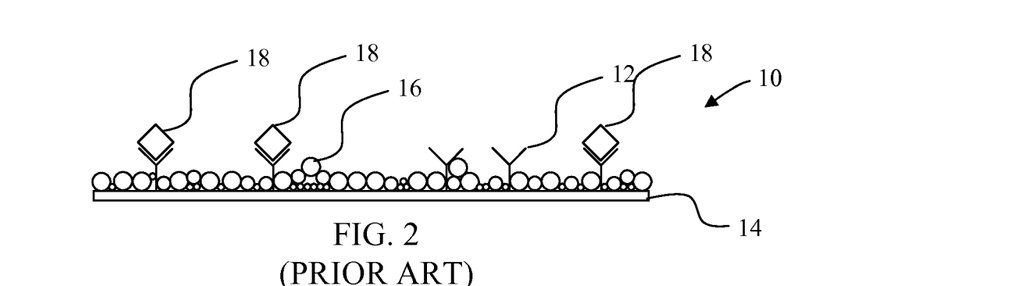
FIG. 2 depicts the test site of FIG. 1 with a molecule of interest bound to some of the antibodies of FIG. 1 after the test site has been incubated and washed.

ELISA plates and microarrays (e.g., Nucleic Acid, peptide, and protein) incorporate a similar principal. FIG. 1 depicts an ELISA assay 10 wherein antibodies 12 are immobilized on a substrate 14. The substrate 14 may be positioned within a well (not shown). A blocker 16 is provided to cover the surface of the substrate around the antibody 12. In a typical ELISA assay, a sample including molecules of interest 18 is then added to the well in which the primary antibody 12 is immobilized. Next, the sample is incubated for some time. During incubation, the blocker 16 prevents the molecules of interest in the sample from binding to the surface of the substrate 14 in order to avoid false binding. During incubation, some of the molecules of interest 18 become bound with some of the antibodies 12 as depicted in FIG. 2. After incubation, the remaining sample is washed to remove the unbound molecules of interest 18.

Figure 3:
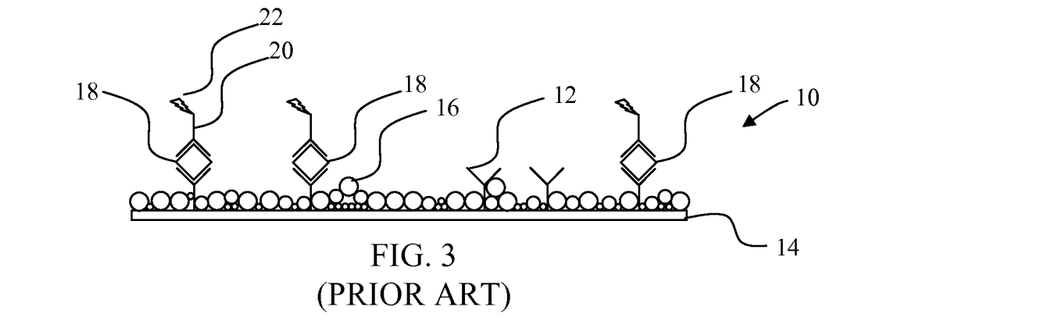
FIG. 3 depicts the test site of FIG. 2 after a labeled secondary antibody has been added and the test site has again been incubated and washed so that the labeled secondary is bound to the bound molecules of interest.

Subsequently, a secondary antibody 20 with a bound label 22 is added to the well, incubated, and washed resulting in the configuration of FIG. 3. As depicted in FIG. 3, the labeled secondary antibodies 20 are bound to the molecules of interest 18 that are in turn bound to the antibodies 12. Accordingly, the number of labels 22 bound by the antibodies 20 to the molecules of interest 18 is proportional to the concentration of the target antigen. Depending on the label used, the number of labels can be finally detected using colorimetry, amperometry, magnetometry, voltammetry, luminescence, or fluorescence detection. Other label-free antibody processes such as surface plasmon resonance may alternatively be used.

The two main figures-of-merit in a detection assay include sensitivity and cross-reactivity; both of which affect the minimum detectable concentration and the diagnosis error rate. The sensitivity in such tests is generally limited by label detection accuracy, association factor of the antibody-antigen pair, and the effective density of the probe antibody on the surface.

Figure 4:
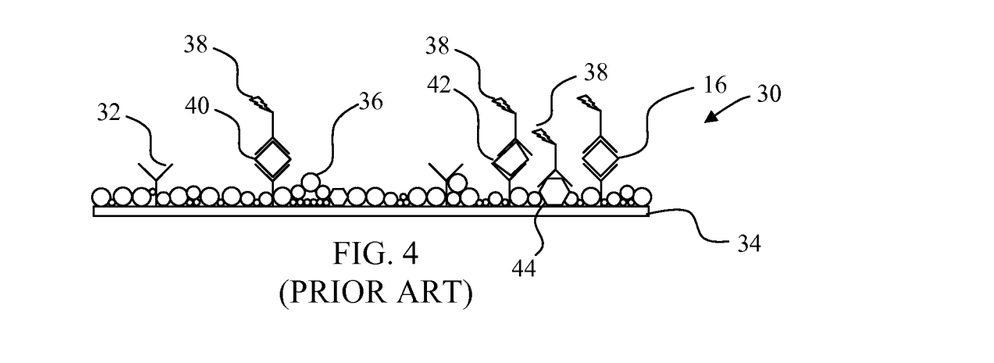
FIG. 4 depicts a schematic of a prior art test site within an ELISA array wherein a labeled secondary is bound to interfering molecules due to cross-reactivity and also physiosorbed to the surface of the substrate raising the background noise level of the test.

One issue that arises with affinity based sensors is the cross-reactivity of the sensor to other biomarkers. In other words, rather than sensing a single biomarker or molecule of interest, a sensor tends to also sense biomarkers other than the biomarker of interest. The cross-reactivity issue is depicted in FIG. 4 wherein an ELISA assay 30 includes antibodies 32 immobilized on a substrate 34 with a blocker 36 covering most of the substrate surface 34. Additionally, a labeled secondary antibody 38 is bound to a molecule of interest 40 which is in turn bound by the primary antibody 32. The labeled secondary antibody 38 has also bound to a molecule 42 which exhibited an affinity for the primary antibody 32 and was labeled by a secondary antibody 38. The sensitivity to a broad range of biomarkers thus increases the false negative/positive rate of diagnostic tests at clinical level as reported, for example, by P. A Benn et al., "Estimates for the sensitivity and false-positive rates for second trimester serum screening for Down syndrome and trisomy 18 with adjustment for cross identification and double positive results," *Prenatal Diagnosis*, Vol. 21, No. 1, pp 46-51, 2001. The presence of other molecules (secondary molecules or antigens) in the sample thus affects the minimum detectable concentration by binding to the primary antibody.

The accuracy of the assay may further be affected by physiosorption. As further depicted in FIG. 4, some features 44 present in the ELISA assay 30, either contaminants or simply an incongruity, may also be bound to a labeled secondary antibody 38. The physiosorbed labeled secondary antibody 38 thus causes an increased background signal.

Provision of diagnostic tests with a high fidelity is further complicated by the relative scarcity of the molecules of interest in a particular sample. As reported by Robert F. Service, "PROTEOMICS: Proteomics Ponders Prime Time," *Science* 321, no. 5897 (Sep. 26, 2008): 1758-1761, the concentrations of different proteins in blood varies by more than 10 orders of magnitude. Thus, to ensure a desired level of fidelity, the affinity of the capture molecule to the biomarker of interest must be orders of magnitude higher than the affinity of the capture molecule to any other molecule in the sample.

Overcoming the cross-reactivity and background problems can significantly delay development of a new assay test and can increase the cost and complexity of the overall test. For example, in an effort to mitigate the various sensitivity and interference issues involved with affinity based testing, a particular assay is typically optimized by finding a combination of reagents and environmental conditions that maximizes the binding of the molecule of interest to the antibody. Thus, optimization can entail incorporating highly selective antibodies. Accordingly, a typical development of an ELISA assay requires several scientists working for more than a year to identify an acceptable antibody. Cross-reactivity of proteins is a common source of the failure of such development efforts.

Another approach for optimizing the diagnostic test for a particular molecule of interest entails controlling the test conditions locally at different sites of the platform to increase the specificity of the tests. One such approach is described in U.S. patent application Ser. No. 12/580,113, filed on Oct. 15, 2009, the entire contents of which are herein incorporated by reference. Control of the test conditions locally at different sites of the platform can also be used to increase the dynamic range of the assay as described in U.S. patent application Ser.

No. 12/688,193, filed on Jan. 15, 2010, the entire contents of which are herein incorporated by reference.

Control of the test conditions locally at different sites of the platform has generally been attempted by electrically influencing biochemical reactions. Various attempts at such electrical control have been reported by R. G. Sosnowski et al., "Rapid determination of single base mismatch mutations in DNA hybrids by direct electric field control," *Proceedings of the National Academy of Sciences of the United States of America* 94, no. 4 (Feb. 18, 1997), Ian Y. Wong and Nicholas A. Melosh, "Directed Hybridization and Melting of DNA Linkers using Counterion-Screened Electric Fields," *Nano Letters* 0, no. 0 (January), Ian Y. Wong, et al., "Electronically Activated Actin Protein Polymerization and Alignment," *Journal of the American Chemical Society* 130, no. 25 (Jun. 1, 2008): 7908-7915, and Ulrich Rant et al., "Switchable DNA interfaces for the highly sensitive detection of label-free DNA targets," *Proceedings of the National Academy of Sciences* 104, no. 44 (Oct. 30, 2007): 17364-17369, among others.

Controlling test conditions by electrically influencing biochemical reactions, while promising, is problematic. For example, most of the electrical potential is dissipated at the electric double layer formed over the electrode surface. Accordingly, the electrical influence has a limited range of effectiveness.

A need exists for a device and method of performing an assay incorporating low cost antibodies. A further need exists for tests such as multiplexed assays, e.g., protein arrays, competitive assays, or bead based arrays, as well as low cost devices, e.g., lateral flow devices, or other biochips. They all provide accurate results and a method of using such arrays. Methods and devices which provide more accurate results than so-called optimized assays would be a further benefit.

SUMMARY

In accordance with one embodiment, a system and method of indirectly modifying an environmental condition at a test site in one embodiment includes providing a test site on a substrate, providing a first activatable stimulant at the test site, providing an actuator configured to activate the first activatable stimulant at the test site, controlling the actuator to activate the first activatable stimulant, and modifying the local chemical environment at the test site with the first activated stimulant.

In accordance with another embodiment, a system for controlling an environmental condition at a test site includes a substrate including at least one test site, at least one activatable stimulant on the substrate and configured for use at the at least one test site, and at least one actuator positioned to actuate at least one of the at least one activatable stimulant at the at least one test site.

DESCRIPTION

For the purposes of promoting an understanding of the principles of the invention, reference will now be made to the embodiments illustrated in the drawings and described in the following written specification. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains.

Figure 5:
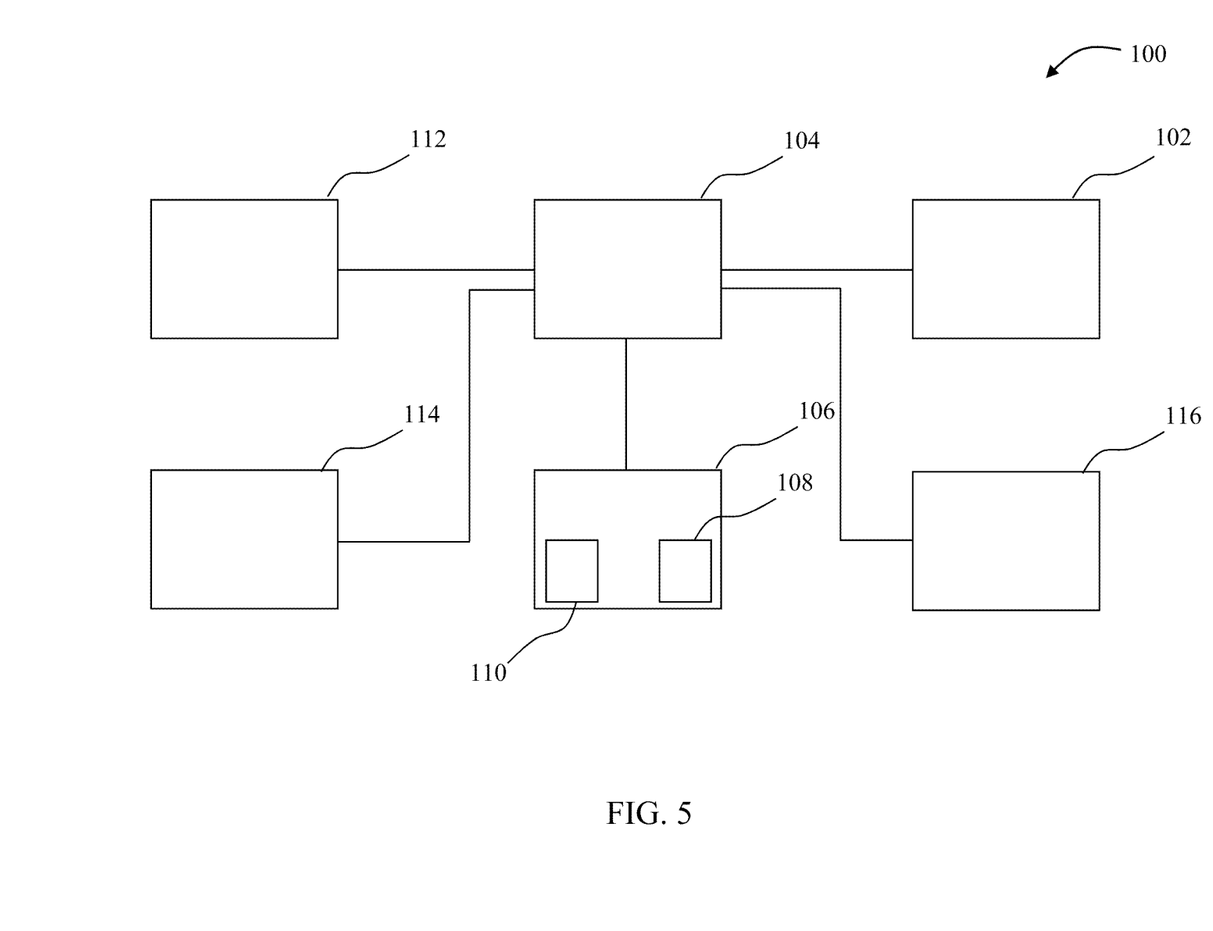
FIG. 5 depicts a multi-site biosensor system configured to control chemical environmental conditions at various test sites to modulate the affinity at the test sites for a molecule of interest.

Referring to FIG. 5, there is depicted a representation of a multisite biosensor system generally designated 100. The biosensor system 100 includes an I/O device 102, a processing circuit 104 and a memory 106. The I/O device 102 may include a user interface, graphical user interface, keyboards, pointing devices, remote and/or local communication links, displays, and other devices that allow externally generated information to be provided to the biosensor system 100, and that allow internal information of the biosensor system 100 to be communicated externally.

The processing circuit 104 may suitably be a general purpose computer processing circuit such as a microprocessor and its associated circuitry. The processing circuit 104 is operable to carry out the operations attributed to it herein.

Within the memory 106 are various program instructions 108. The program instructions 108, some of which are described more fully below, are executable by the processing circuit 104 and/or any other components of the biosensor system 100 as appropriate. Affinity databases 110 are also located within the memory 106.

The biosensor system 100 further includes chemical environment actuator equipment 112 and chemical environment detector suite 114. The chemical environment actuator equipment 112 is configured to activate an activatable stimulant that affects the chemical environmental conditions at a test site, in this example, within a microarray 120 depicted in FIG. 6. Various methods may be used to form the microarray platform 120. By way of example, U.S. Pat. No. 5,807,522 discloses a method for forming microarrays.

Figure 6:
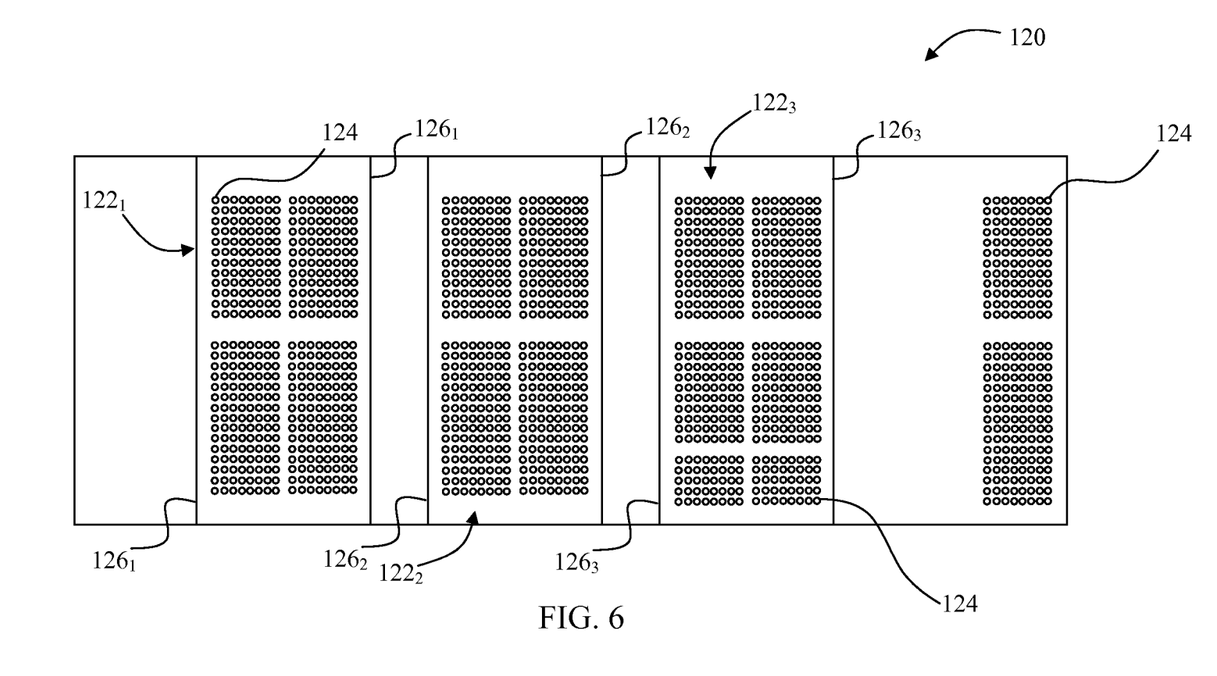
FIG. 6 depicts a platform for providing a number of different test sites in the form of a microarray.

The microarray platform 120 includes a number of different subarrays 122$_x$. The subarrays 122$_x$ include a number of test sites 124. Each of the subarrays 122$_x$ is associated with a respective electrode pair 126$_x$. The number and layout of subarrays 122$_x$ and associated electrode pairs 126$_x$, as well as the number of test sites 124 within each of the subarrays 122$_x$ may be varied within the scope of the invention. In this embodiment, the chemical environment actuator equipment 112 is operable to establish a voltage profile within the microarray platform 120 using the electrode pairs 126$_x$. The chemical environment actuator equipment 112 is thus used to control the pH at each of the test sites 124 as described more fully below. The precise pH within each of the test sites 124 may be detected by the detector suite 114. Sensors may be provided on the microarray platform 120 to assist in determining the precise pH within each of the test sites 124.

The system 100 further includes a label reader 116. The label reader 116 may be included in a single device along with the other components of the system 100. Alternatively, one or more of the components of the system 100 may be provided as a separate device which may be remotely located from the other components of the system 100.

The test sites 124 are prepared with a capturing agent effective for capturing a biomolecule of interest. Further details regarding the biosensor system 100 are provided with reference to the procedure 130 of FIG. 7. The processor 104 executes the program instructions 108 to execute at least some of the procedure 130 of FIG. 7. In different embodiments, the procedure 130 may be modified to include more or fewer steps depending upon the specific criterion.

Figure 7:
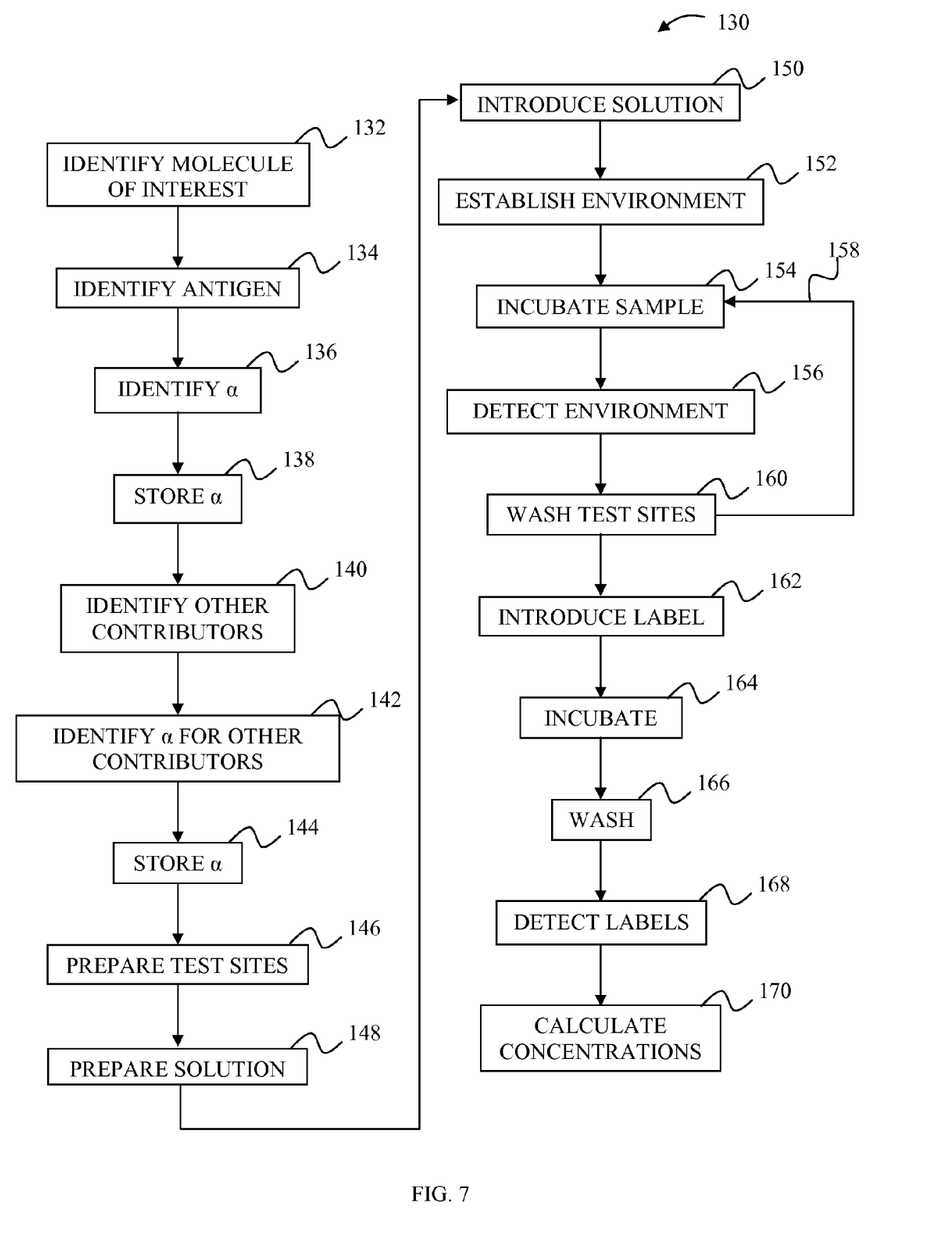
FIG. 7 depicts a procedure that can be used to indirectly establish different test chemical environments at various test sites on a platform so as to expose a sample to multiple test environments.

At block 132 of FIG. 7, a molecule of interest is identified and then an antibody with an affinity for the molecule of interest is identified (block 134). A binding efficiency coefficient for the molecule of interest (a) with the identified antibody is then identified for a variety of different chemical environmental conditions (block 136) and stored in one of the affinity databases 110 (block 138).

Potential sources of test signal interference or noise likely to be present in a tested sample are then identified (block 140). The identification of signal interference may include, for example, an identification of likely or potential molecules within a sample that also have an affinity for the identified antibody. A binding efficiency coefficient for each source of noise ($\alpha_n$) with the identified antibody is then identified for each of the different chemical environmental conditions (block 142) and stored in one of the affinity databases 110 (block 144).

At block 146, the microarray platform 120 is prepared by depositing the desired amount of the selected capturing agent in each of the test sites 124. In alternative embodiments, a subset of the test sites 124 may be prepared with a first capturing agent while another subset of the test sites 124 may be prepared with a second capturing agent so as to allow two separate tests to be conducted within a single microarray platform 120. Additional configurations within a single microarray platform 120 may also be used. By way of example, each of the test sites within one of the subarrays 122 may be prepared with the same capturing agent while each of the subarrays 122 includes a different capturing agent. The number of test sites 124 prepared with a particular capturing agent in this embodiment is selected to be at least the same as the number of noise sources identified above plus the molecule of interest.

Once the microarray platform 120 is prepared, a bulk solution is prepared (block 148). The bulk solution includes the sample that is to be tested along with an activatable stimulant. An "activatable stimulant" as that term is used herein is a substance that can exist within a bulk solution in an inactive state and which can be activated while in the bulk solution by an actuator into an active state wherein chemical conditions in the bulk solution are altered.

One such activatable stimulant which can be used to modify the pH of a bulk solution is an amphoteric electrolyte. Amphoteric electrolytes are composed of salt ions that have both acidic and basic chemical groups. The presence of both chemical groups allows the electrolyte to protonate and deprotonate at the same time. Protonation and deprotonation affects the acid dissociation constant ($K_a$, or, when expressed as a logarithm, $pK_a$) of the amphoteric electrolyte. Specifically, equilibrium of the proton donor reaction of an amphoteric electrolyte can be written symbolically as:

while equilibrium of the proton acceptor reaction of the amphoteric electrolyte can be written symbolically as:

wherein HA is the generic amphoteric electrolyte, A− is the conjugate base, and H+ is the hydronium acid molecule. The amphoteric electrolyte is in equilibrium when the concentrations of the HA, A−, and H+ components do not change. This constant is represented by the following equation:

$$K_a = \frac{[A^-][H^+]}{[HA]}$$

Thus, $$pK_a = \log_{10} \frac{[A^-][H^+]}{[HA]}$$

At a given pH, an amphoteric electrolyte will achieve an equilibrium concentration of the HA, A−, and H+ components that operates at the lowest internal energy of the system. Upon application of an external source of energy, such as a voltage applied across electrodes immersed in the bulk solution, a new equilibrium concentration ($pK_a$) will be achieved according to Le Chatelier's Principle.

More specifically, when an amphoteric electrolyte molecule accepts a proton (H+), the remainder of the amphoteric electrolyte molecule has a positive charge. Similarly, when an amphoteric electrolyte molecule loses a positive ion (H+), the remainder of the amphoteric electrolyte molecule has a negative charge. Thus, when the amphoteric electrolyte is at equilibrium, there will be an equilibrium concentration of negatively charged amphoteric electrolyte molecules and positively charged amphoteric electrolyte molecules.

Introduction of a negative voltage by a negatively charged electrode raises the internal energy of the system by entropic effects as the concentration of the positively charged amphoteric molecules in the electrode vicinity rises above that in the bulk liquid. The higher internal energy provides a driving force for the deprotonation of the positively charged amphoteric electrolyte molecules according the to proton acceptor equation above resulting in a lower concentration of the positively charged amphoteric electrolyte molecules at a new equilibrium.

Deprotonation of the positively charged amphoteric electrolyte molecules under the influence of a negative electrode thus raises the relative concentration of the H+ ions in the area proximate the negatively charged electrode. As the H+ concentration increase, the pH necessarily decreases. Accordingly, the amphoteric electrolyte can exist within the bulk solution in an inactive state and can later be activated while in the bulk solution by an electrode into an active state wherein the pH in the bulk solution proximate the electrode is altered.

Returning now to the procedure 130 of FIG. 7, once the bulk solution is prepared (block 148), the bulk solution is introduced into the selected set of test sites 124 (block 150). The chemical environment actuator equipment 112 is then controlled to apply the desired voltage or voltages across the electrode pairs $126_x$ which activates the activatable stimulant in the bulk solution and, in this embodiment, causes the pH to be modified at the test sites 124 (block 152).

The sample is then incubated at the established test environment for a predetermined time (block 154). During the incubation, the actual test environment within each of the selected set of test sites 124 is monitored by the environment detector suite 114 and data indicative of the established test environment is provided to the processing circuit 104 (block 156).

In one embodiment, data obtained at block 156 is passed to the processing circuit 104 (block 158). Under control of the processing circuit 104, the electrodes $126_x$ can be controlled to further modulate the pH at each of the test sites 124. Alternatively, lookup tables may be stored in the memory 106 wherein particular pH values are associated with electrode voltages for particular concentrations of amphoteric electrolytes.

When the sample has been sufficiently incubated, the test sites 124 are washed (block 160) and a labeled secondary antibody is introduced into the selected set of test sites 124 (block 162) and incubated (block 164). The selected set of test sites 124 are then washed (block 166) and the labels remaining in the test sites 124 are detected by the label reader 116 (block 168). Based upon the signals associated with the number of labels remaining in the selected set of test sites 124, the concentration of one or more molecules of interest within the sample is calculated by the processing circuit 104 (block 170).

Figure 8:
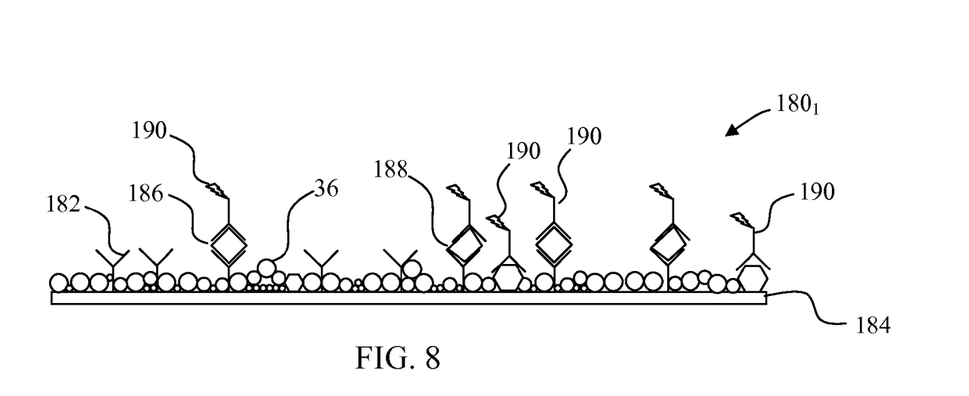
FIG. 8 depicts a schematic of a test site wherein a labeled secondary is bound to molecules of interest, to interfering molecules due to cross-reactivity, and also physiosorbed to the surface of the substrate raising the background noise level of the test.

Calculation of the concentration of one or more molecules of interest is possible since the signal obtained by the label reader 116 for a particular one of the selected set of test sites 124 is the summation of the contributors to the signal including the molecule of interest, and each of the noise sources such as interfering molecules. By way of example, FIG. 8 depicts a test site $180_1$ including antibodies 182 formed on a substrate 184. Antigen 186 has been bound to some of the antibodies 182. Some interfering antigen 188 has also bound to some of the antibodies 182. A labeled secondary antibody 190 has bound to each of the bound antigens 186 and each of the bound interfering antigens 188. Some of the labeled secondary antibody 190 has also physiosorbed to the blocked surface of the substrate 184.

Figure 9:
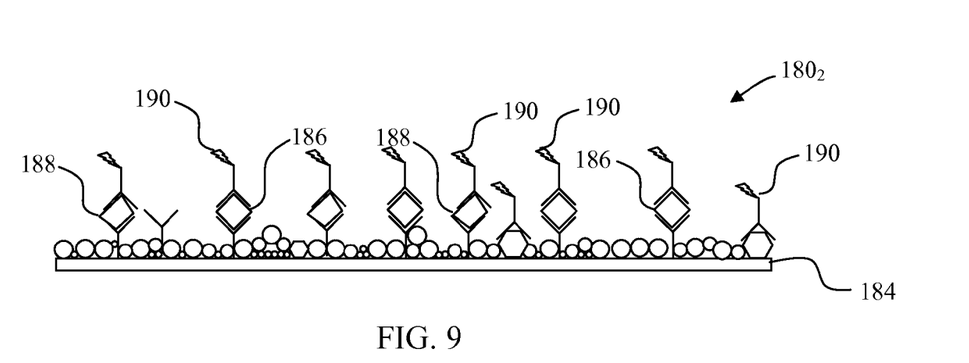
FIG. 9 depicts a schematic of a test site formed identically to the test site of FIG. 8 and exposed to the same sample to which the test site of FIG. 8 was exposed, but maintained at a pH different from the pH of the test site of FIG. 8 during incubation, resulting in different binding efficiencies for the different signal contributors.

The relative proportion of the signal attributable to each of the contributors is dependent upon the concentration of the particular contributor, the concentration of the other contributors, and the relative affinity to the initially deposited capturing agent of each of the contributors. The relationship is reflected in the following equation:

$$S_1 = \alpha_{1\text{-}1}C_1 + \alpha_{1\text{-}2}C_2 + \ldots \alpha_{1\text{-}x}C_x$$

wherein $S_1$ is the signal associated with the detected label in a first of the test sites 124, $\alpha_{1\text{-}1}$ is the binding efficiency proportional to affinity for the identified contributor (1 through x) at the environment established in the first of the test sites 124, and C is the concentration in the sample of the identified contributor (1 through x). Accordingly, because the number of the selected set of test sites 124 is equal to at least the number of interfering contributors plus one, the number of detected signals will correspond to the number of identified interfering contributors plus the molecule of interest. The contribution of the various sources to the overall signal, as well as the value of the overall signal, will vary from test site to test site. For example, FIG. 9 depicts a test site $180_2$ which was prepared identically to the test site $180_1$ and exposed to a sample identical to the sample used with the test site $180_1$. The test environment in each of the test sites $180_x$ was different. Accordingly, the labeled secondary antibody 190 bound to the molecule of interest has increased from two in FIG. 8 to four in FIG. 9. Additionally, the labeled secondary antibody 190 bound to the interfering antigen has increased from two in FIG. 8 to three in FIG. 9.

Thus, if three noise contributors are identified in a sample, such as analytes that bind non-specifically to primary antibody sites and prevent the biomarker to bind, analytes that form a sandwich and produce erroneous signals, and analytes that physisorb to the surface of the test site and produce erroneous signals, along with the molecule of interest, four test sites, such as four of the test sites 124, are the minimum number of cells prepared at block 144. Therefore, four signals will be obtained, as reflected in the following equations:

$$S_1 = \alpha_{1\text{-}1}C_1 + \alpha_{1\text{-}2}C_2 + \alpha_{1\text{-}3}C_3 + \alpha_{1\text{-}4}C_4$$

$$S_2 = \alpha_{2\text{-}1}C_1 + \alpha_{2\text{-}2}C_2 + \alpha_{2\text{-}3}C_3 + \alpha_{2\text{-}4}C_4$$

$$S_3 = \alpha_{3\text{-}1}C_1 + \alpha_{3\text{-}2}C_2 + \alpha_{3\text{-}3}C_3 + \alpha_{3\text{-}4}C_4$$

$$S_4 = \alpha_{4\text{-}1}C_1 + \alpha_{4\text{-}2}C_2 + \alpha_{4\text{-}3}C_3 + \alpha_{4\text{-}4}C_4$$

Each term is thus proportional to a binding efficiency factor, $\alpha$, which is a function of the molecule affinities and other assay conditions, e.g., mass transport. Accordingly, because the same sample is used in each of the test sites 124, and because the binding efficiency of the molecule of interest and the interfering antigens for the specific chemical environment in each of the test sites 124 is known, the procedure 130 provides four equations and four unknowns. The concentrations of each of the contributors can thus be ascertained in a known manner. Accordingly, the concentrations of multiple molecules of interest within a sample can also be ascertained. In practice the signals are noisy and linear estimation algorithms may be used to estimate the value used for any particular signal. Additionally, one or more sensor sites may be used as a control site to improve the accuracy of the procedure 130.

In the foregoing procedure, the thermodynamic properties of amphoteric electrolytes was used which allows modulation of protein affinity with small biases (e.g., <1V) and long experiment time (e.g., about 2.5 hours). This approach is contrasted with other approaches which are based on the rate of transport of charged nucleic acid in solution. By way of example, Leroy Hood et al., "Systems Biology and New Technologies Enable Predictive and Preventative Medicine," Science 306, no. 5696 (Oct. 22, 2004): 640-643, describes electrical modulation of nucleic acid hybridization based on the rate of transport of charged nucleic acid in solution. In this transport modality, amphoteric ions have the property of decreasing solution conductivity such that more potential energy can be transferred to the bulk solution at the double layer interface. As a result, the previously reported experiments could only be performed over short times (~30 s) with large bias (~3V) as reported by C. F. Edman et al., "Electric field directed nucleic acid hybridization on microchips," *Nucl. Acids Res.* 25, no. 24 (Dec. 15, 1997): 4907-4914.

An example of an amphoteric molecule which can be used in the procedure 130 is β-alanine, which has a molecular formula of $C_3H_7NO_2$. β-alanine is a naturally occurring amino acid that has the amino group at the β-position from the carboxylate group. It is a non-essential amino acid, and is very soluble in water. Due to the presence of both amine and carboxylic acid groups, β-alanine is capable of protonating and deprotonating at the same time, with pKa values of 3.6 and 10.2 respectively. These reactions are represented by the following equations:

$$\beta \leftrightarrow \beta^- + \beta^- + H^+ (pK_a=3.6)$$

$$\beta^+ \leftrightarrow \beta + H^+ (pK_a=10.2)$$

Therefore, the concentrations at equilibrium are

By selecting the correct pH, it is thus possible to deprotonate more carboxylate groups than protonating anime groups, resulting in a net imbalance of [β+] and [β−]. For instance, [β−]=2510[β] and [β+]=1580[β] at pH 7. Hence, there is approximately 60% more [β−] than [β+], which yields about 23% β-alanine in the form of only β−, with the rest in the form of zwitterions that contain both β+ and β− groups (assuming complete ionization). If the initial pH is selected at 8, then 98% of β-alanine would be in the form of only β−, and the rest in the form of zwitterions.

Accordingly, with the application of an electrical potential across two electrodes in a solution, the β− ions would be attracted to the positive electrode, and a local high concentration of the β− ions would be built up about the positive electrode. As a result, the [β−] at the positive electrode could be more than doubled compared to the bulk solution. Because of the equilibrium relations described above, an increase in [β−] would push the chemical reaction to the [β] side according to Le Chatelier's Principle, causing a reduction in the local [H+] concentration.

Thus, the local pH at the positive electrode is modulated dynamically in response to the applied potential, and therefore, the protein affinity can be indirectly modulated. β-alanine is just one example of amphoteric ions that is capable of altering local pH at the electrode vicinity. To provide enhanced pH modulation ability, amphoteric ions with pKa values close to pH 7 may be used. Such amphoteric ions favor an uncharged state at equilibrium. With the accumulation of single-charged ions, it is more likely for the ions to convert back to the uncharged state, releasing or consuming H+ ions along the way for pH modulation.

The use of an amphoteric electrolyte to indirectly modulate the pH in the area about an electrode has been experimentally verified using a system incorporating Indium Tin Oxide (ITO) electrodes fabricated on a glass slide by an etching process. The glass slide with the etched electrodes was then provided with a surface functionalization treatment by MicroSurfaces, Inc., of Austin Tex., to form a poly-ethyleneglycol (PEG) film anchored to the glass slide by silane coupling chemistry. In the experiment, antibody fragments (Immuno ChromPure Mouse IgG Fragment Fc, available from Jackson ImmunoResearch, West Grove, Pa.) were spotted on functionalized surfaces (NHS2, Microsurfaces Inc, Austin Tex.) which were subsequently incubated at three different voltages (0.0V, 0.25V and 0.5V) with an anti-mouse antibody (goat anti-mouse IgG H+L DyLight 549-conjugated, available from Jackson ImmunoResearch, West Grove, Pa.) to assess affinity to the IgG. The samples were then washed and read using an Axon Fluorescent scanner (commercially available from MDS Analytical Technologies, Sunnyvale, Calif.).

Three samples were used in the experiment. A first sample was used to provide a baseline reading. A second sample included PBS/PBS Tween 20, available from Sigma Aldrich, St. Louis Mo., in the incubation/washing buffer. A third sample included PBS/PBS Tween 20 mixed with 500 mM β-alanine, commercially available from Sigma Aldrich, St. Louis Mo., in the incubation/washing buffer.

Figure 10:
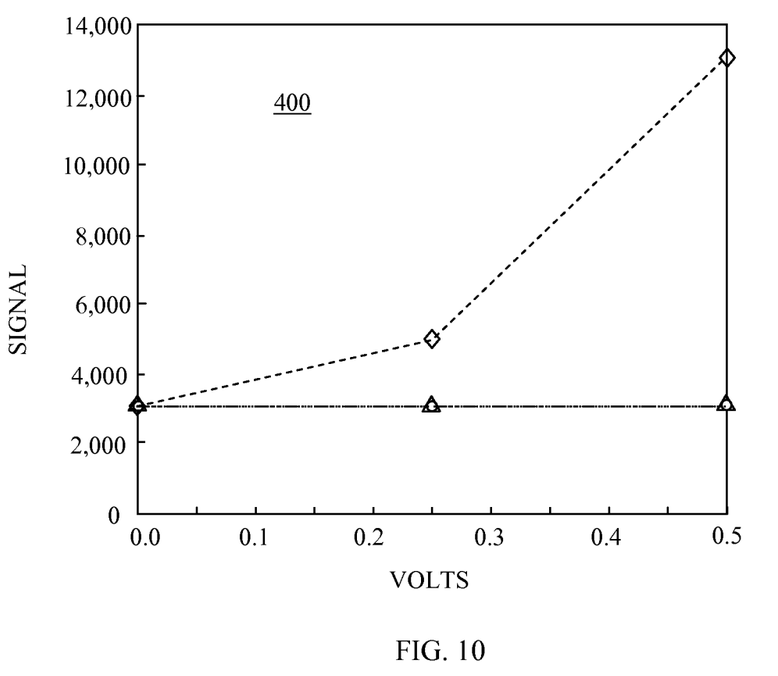
FIG. 10 depicts a graph of a detected signal for three samples of the same concentration of a molecule of interest at different voltages showing the effect on the affinity between the capture molecule at a test site and the molecule of interest when an activatable stimulant is activated by an electrode to modify the chemical environment at the test site.

The results of the above described experiment are depicted in the graph 400 of FIG. 10 which depicts the normalized values obtained with the experiment. In FIG. 10, the readings of the first sample at 0.0V, 0.25V and 0.5V are indicated by a circle, the readings from the second sample are indicated by a triangle, and the readings using the third sample are indicated by a diamond. The graph 400 indicates that there were no significant differences in the readings between the baseline sample at the different voltages with a signal of about 3,000 counts, and a background noise level that was determined to be about 30 counts using the equations set forth above. Additionally, no noticeable change from the baseline measurements was obtained using the second sample at any of the three voltages.

Significant changes, however, were obtained with the third sample. At 0.0V, the graph 400 shows that a reading of 3000 counts was obtained. The graph 400 thus indicates that the addition of the β-alanine alone did not significantly alter the reading of the sample since the baseline sample also produced a reading of 3000 counts as discussed above. When a voltage of 0.25V was applied, the readings obtained from the third sample increased to a count of 5,000. A further increase was obtained by increasing the voltage to 0.5V. At 0.5V, a reading of about 13,000 counts was obtained. Additionally, the background contribution to the 13,000 counts was determined to be about 150 counts. Thus, by applying a voltage to the electrode actuators, the β-alanine was activated with a resultant change in pH that increased the affinity of the test sites by a factor of more than 4 while the noise increased by a factor of 3.

While the foregoing experiment shows that amphoteric electrolytes can be used as an activatable stimulant which can be activated by electrodes, an activatable stimulant can take other forms. By way of example, R. Ferrari, "Cancer nanotechnology: Opportunities and challenges," *Nat. Rev. Cancer*, vol. 5, pp. 161-171, 2005, discusses the use of a polymeric polyelectrolyte material to encapsulate a reactive biomolecule. By incorporating a "layer-by-layer" (LbL) technique, as discussed by E. Donath, et al., "Novel hollow polymer shells by colloid-templated assembly of polyelectrolytes," *Angew Chem., Int. Ed., vol.* 37, pp. 2201-2205, 1998, precise tailoring of the shell for a microcapsule is possible. In the LbL technique, alternate adsorption of oppositely charged polyelectrolytes on various colloidal templates is used to provide, e.g., precise encapsulation thicknesses.

The control available using LbL techniques further allows precise engineering of the physical properties of the encapsulation shell. For example, G. Ibarz, et al., "Resealing of polyelectrolyte capsule after core removal," *Macromol Rapid Commun*, vol. 23, pp. 474-478, 2002, discusses the modulation of the mechanical strength of encapsulation shells by varying the number of layers in the shell. Additionally, chemical characteristics of the encapsulation shell can be varied as discussed by B. DeGeest, "Intracellularly degradable polyelectrolyte microcapsules," *Adv Mater*, vol. 18, pp. 1005-1009, 2006.

Accordingly, a stimulant can be encapsulated and included into a bulk solution including a sample. When desired, an actuator can then be controlled to form a breach in the layers formed about the stimulant thereby releasing the stimulant into the bulk solution so as to modify the chemical environment at a test site.

The form of the actuator can be varied depending upon the particular embodiment of the microcapsule. In one embodiment, an ultrasonic resonator may be used to break apart the microcapsule. The use of an ultrasonic resonator is discussed by B. DeGeest, et al., "Ultrasound-triggered release from multilayered capsules," *Small*, vol. 3, pp. 804-808, 2007.

When using an ultrasonic resonator, microcapsules with different shell mechanical properties may be incorporated into a bulk solution. The use of different shell mechanical properties allows for selective fracture of the microcapsule shells to allow for selective increase in the amount or type of stimulant released into the bulk solution. Selective release of encapsulated materials has been discussed by B. DeGeest, et al., "Ultrasound-triggered release from multilayered capsules," *Small*, vol. 3, pp. 804-808, 2007.

Thus, stimulants may be embedded into $CaCO_3$ microparticles and coated with alternating layers of polyelectrolytes with gold nanoparticles to provide for selective release of the stimulants. Microparticles fabricated in this fashion were shown to have varying release efficiencies with ultrasound at 20 kHz based on the power output of the resonator (20-100 W) as well as the time applied (1-10 seconds).

If desired, the encapsulated stimulants may be of varying types, each type having a shell with a different activation characteristic. For example, pH buffers of increasing acidity can be encapsulated in microcapsules with increasing shell thicknesses. Thus, by increasing the power output of an ultrasonic resonator, a larger, more dramatic release of pH buffer will be introduced to the system. In a similar fashion, microcapsule shells may also be tuned to be activated by different resonant frequencies, with the ensuing bulk modulation relying on the frequency output rather than just the power of the resonator.

Other actuators that may be used with microcapsule type activatable stimulants include LASER devices. A LASER can be used to heat metallic nanoparticles within a microcapsule shell. The embedded nanoparticles absorb the energy and disrupt their local environment, resulting in destructive changes in permeability in the outer shell as discussed by S. Skirtach, et al., "The role of metal nanoparticles in remote release of encapsulated materials," *Nano Letters*, vol. 5, pp. 1371-1377, 2005.

A multisite biosensor can thus be implemented on a printed circuit board, glass, plastic substrate, or on a CMOS chip with gold, glass, epoxy, polymer, or gel coating, or even in a well plate such as a 96 well plate. If desired, control, readout, and also sensing for the control can be provided in the printed circuit board or CMOS chip. CMOS technology allows multiple sensing sites to be fabricated in close proximity. This assists in maintaining uniformity of non-controlled environmental factors amongst the test sites. The chip can be part of a system using stand alone microfluidics or a capillary principle or may be used with a separately provided device. The signal estimation and the assay data can be hard coded on the CMOS chip if desired.

Moreover, the activatable stimulant may be provided on the same substrate as the test site and mixed with the sample as the sample is transported to the test site. For example, a substrate may include a sample receiving area that is linked to a test site by a fluid path. The activatable stimulant may be prepositioned at a location on the fluid path such that the activatable stimulant mixes with the sample as the sample moves toward the test site.

The biosensor system 100 may thus incorporate a variety of activatable stimulants which, when activated, modify the chemical environment of a test site. The particular molecule of interest will vary depending upon the particular embodiment. Likewise, the type of sensor or sensors incorporated into the label reader 116 will vary depending upon the particular label used. Various embodiments may thus use luminescence, fluorescence, colorimetric, electrochemical, impedance, and magnetic sensors. The sensors can be configured to allow isolation of the signal produced by a selected one or more test sites. Likewise, the sensors incorporated into the environment detector suite 114 may include IR sensors, and Hall sensors. AMR sensors or GMR sensors may be provided to monitor the density of magnetic beads on a test site surface. ISFETs or CMOS based charge detection circuits may be used in electrochemical embodiments.

The procedure 130 can thus be used in a variety of test site platforms including 96-well plates, plates with fewer or additional wells, microarray platforms, printed circuit board platforms, CMOS chip platforms, multiplexed assays, protein arrays, lateral flow devices, sandwich assays, competitive assays, bead based arrays or other appropriate platforms. The procedure 130 may further be used for the detection of a variety of molecules of interest as well as different types of molecules in addition to antibodies. By way of example, the procedure 130 may also be used for the detection of nucleic acid, protein, or small molecules. The procedure is not limited to binding processes, and can thus be extended to enzymatic reaction studies including phosphorylation studies, protein-protein interactions, protein nucleic acids interactions, and competitive assays.

While the invention has been illustrated and described in detail in the drawings and foregoing description, the same should be considered as illustrative and not restrictive in character. It is understood that only the preferred embodiments have been presented and that all changes, modifications and further applications that come within the spirit of the invention are desired to be protected.

The invention claimed is:

1. A system for controlling a chemical environmental condition at an affinity based test site comprising:
   a substrate including at least one test site;
   at least one activatable stimulant on the substrate and configured for use at the at least one test site; and
   at least one actuator positioned to actuate at least one of the at least one activatable stimulant at the at least one test site such that chemical conditions at the at least one test site are altered thereby modifying an affinity between a capture molecule at the test site and a molecule of interest.

2. The system of claim 1, further comprising:
   a memory;
   a plurality of command instructions stored within the memory; and
   a controller operably connected to the memory and to the at least one actuator and configured to execute the plurality of command instructions to control the at least one actuator to actuate the at least one of the at least one activatable stimulant.

3. The system of claim 2, further comprising:
a sensor operably connected to the controller and configured to sense a chemical environmental condition at the at least one test site, wherein the controller is further configured to execute the plurality of command instructions to control the at least one actuator to actuate the at least one of the at least one activatable stimulant based upon the sensed chemical environmental condition at the at least one test site.

4. The system of claim 3, wherein:
the at least one activatable stimulant comprises a first activatable stimulant and a second activatable stimulant;
the first activatable stimulant is configured to activate in response to a first activation input but not a second activation input; and
the second activatable stimulant is configured to activate in response to the second activation input.

5. The system of claim 4, wherein the at least one actuator comprises at least one resonator.

6. The system of claim 3, wherein the at least one actuator comprises at least one electrode.

7. The system of claim 2, wherein the substrate comprises a CMOS substrate.

8. The system of claim 2, wherein the substrate comprises:
a test sample receiving area spaced apart from the at least one test site; and
a fluid path including the test sample receiving area and extending to the at least one test site, wherein the at least one activatable stimulant is positioned on the substrate such that fluid received by the test sample receiving area and transported along the fluid path entrains the at least one activatable stimulant and transports the at least one activatable stimulant to the at least one test site.

9. The system of claim 8, further comprising:
a reader configured to receive at least the portion of the substrate including the at least one test site, the reader including the memory and the controller.

10. The system of claim 1, wherein the substrate is a glass substrate comprising:
at least one electrode etched on the glass substrate; and
a poly-ethyleneglycol (PEG) film.

11. The system of claim 1, wherein the at least one activatable stimulant comprises one or more of an amphoteric electrolyte and a first type of microcapsule bead.

12. The system of claim 11, wherein the at least one activatable stimulant comprises:
the first type of microcapsule bead; and
a second type of microcapsule bead, wherein the second type of microcapsule bead has an activation characteristic different from an activation characteristic of the first type of microcapsule bead.

13. The system of claim 4, wherein:
the first activatable stimulant comprises a first type of microcapsule bead; and
the second activatable stimulant comprises a second type of microcapsule bead.

* * * * *